(12) United States Patent
Wellisz et al.

(10) Patent No.: US 6,168,596 B1
(45) Date of Patent: Jan. 2, 2001

(54) CRANIAL BONE FLAP FIXATION CLIP

(75) Inventors: Tadeusz Z. Wellisz; Eric V. Hohenstein, both of Los Angeles, CA (US)

(73) Assignee: Bioplate, Inc., Los Angeles, CA (US)

(*) Notice: Under 35 U.S.C. 154(b), the term of this patent shall be extended for 0 days.

(21) Appl. No.: 09/435,645

(22) Filed: Nov. 9, 1999

(51) Int. Cl.⁷ .................................................. A61B 17/80
(52) U.S. Cl. .............................................. 606/69; 606/151
(58) Field of Search .................. 606/69, 70, 71, 606/151

(56) References Cited

U.S. PATENT DOCUMENTS

| | | |
|---|---|---|
| 3,220,081 | 11/1965 | Rector . |
| 4,364,382 * | 12/1982 | Mennen ................................ 606/69 |
| 4,651,724 * | 3/1987 | Berentey et al. ..................... 606/69 |
| 5,201,737 * | 4/1993 | Leibinger et al. .................... 606/69 |
| 5,487,741 | 1/1996 | Maruyama . |
| 5,501,685 | 3/1996 | Spetzler . |
| 5,549,620 | 8/1996 | Bremer . |
| 5,586,985 * | 12/1996 | Putnam et al. ........................ 606/69 |
| 5,669,912 | 9/1997 | Spetzler . |
| 5,718,705 * | 2/1998 | Sammarco ............................. 606/69 |
| 5,797,916 * | 8/1998 | McDowell ............................. 606/69 |
| 5,810,822 * | 9/1998 | Mortier ................................. 606/69 |
| 5,916,217 | 6/1999 | Manthrop et al. ..................... 606/69 |
| 5,941,878 | 8/1999 | Medoff . |
| 5,961,519 * | 10/1999 | Bruce et al. ........................... 606/69 |

FOREIGN PATENT DOCUMENTS

| | | | |
|---|---|---|---|
| 1816443 * | 5/1993 | (SU) | ..................................... 606/69 |
| WO 97/42912 | 11/1997 | (WO) . | |

* cited by examiner

*Primary Examiner*—Paul J. Hirsch
(74) *Attorney, Agent, or Firm*—William W. Haefliger

(57) ABSTRACT

A clip to inter-connect primary and secondary bone zones having edges, comprising in combination a tab to extend over a surface or surfaces of at least one of the bone zones, above a level defined by the one surface; a first projection carried by the tab and having a hook to engage a bone zone at its edge, and below the level.

20 Claims, 4 Drawing Sheets

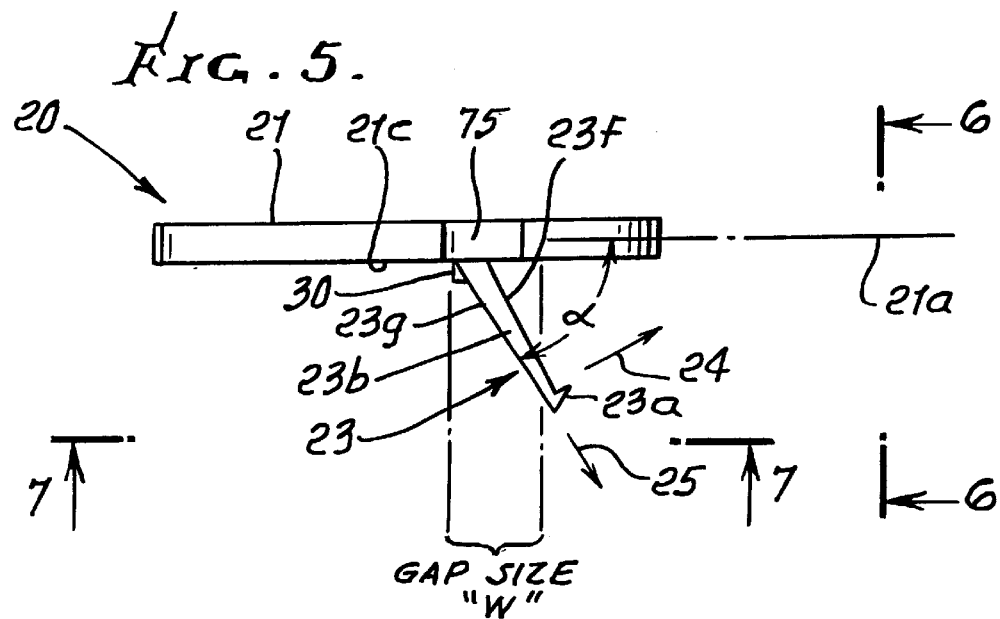
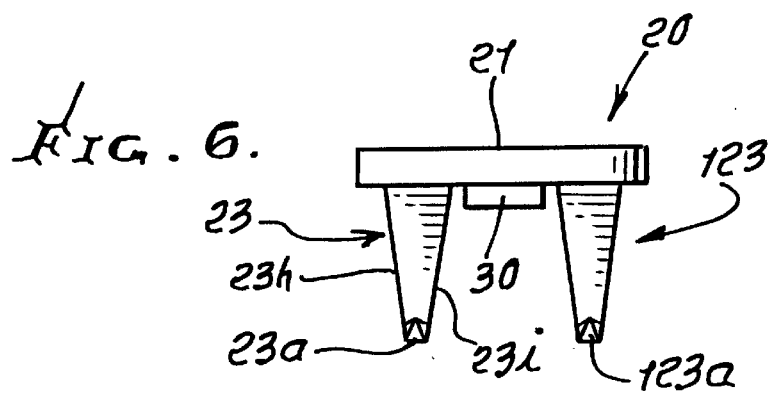
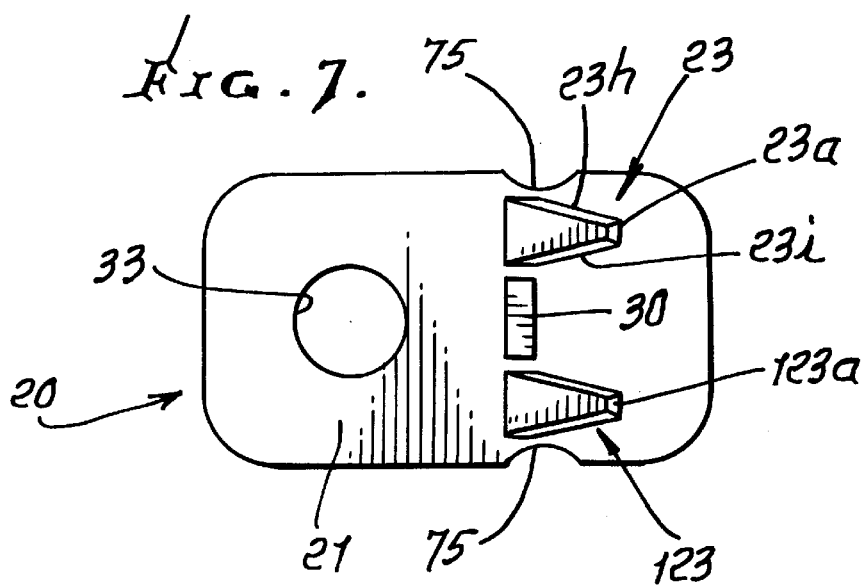

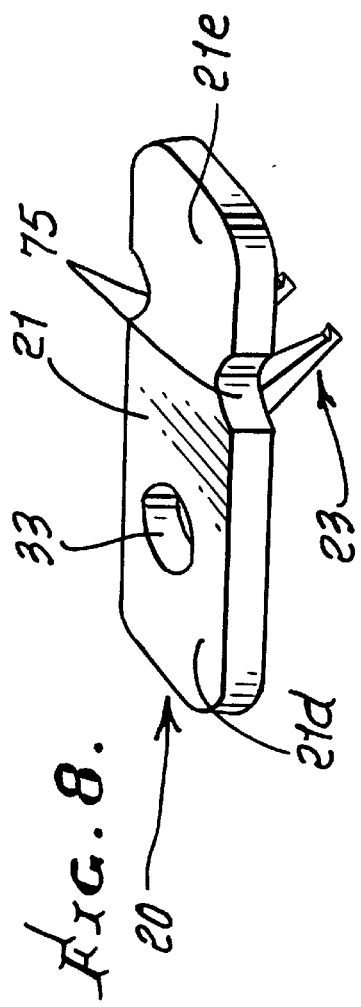
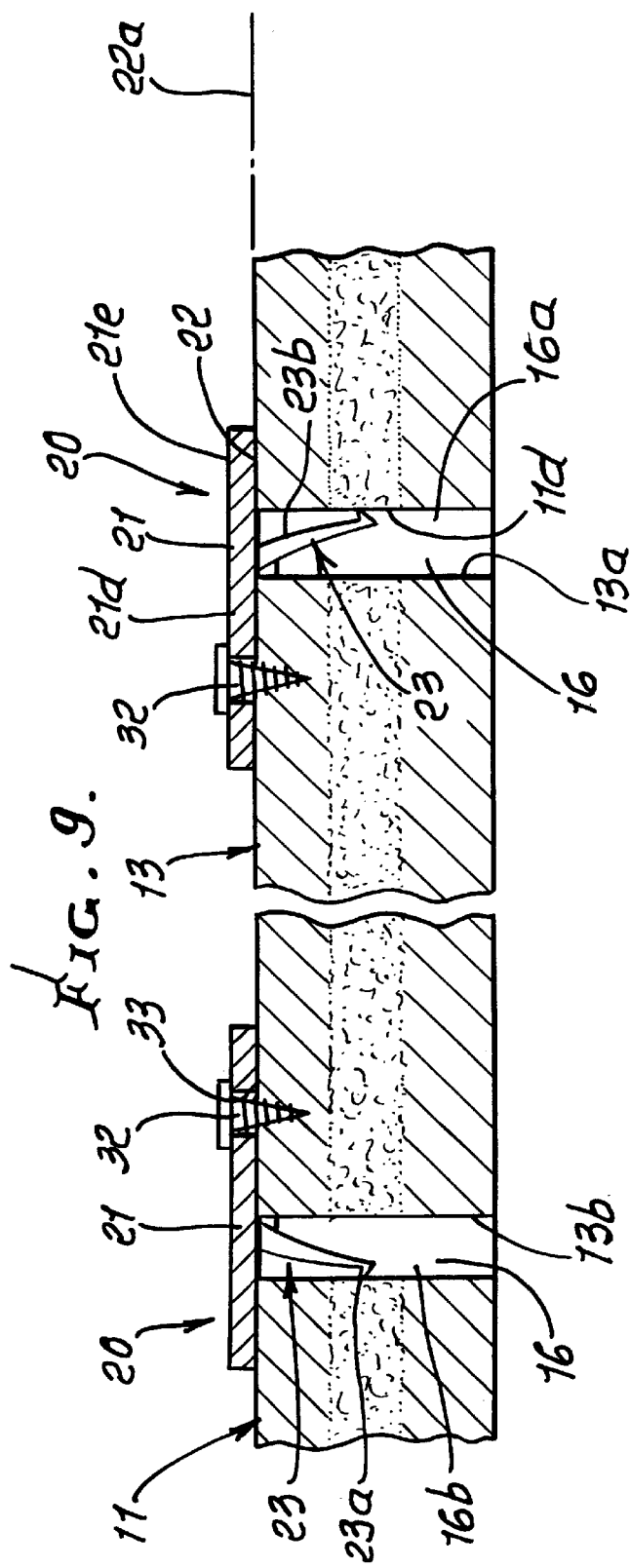

CRANIAL BONE FLAP FIXATION CLIP

BACKGROUND OF THE INVENTION

This invention relates generally to the alignment and fixation of bone segments as required for appropriate bone healing, for example after fracture or surgical intervention, and specifically to a device, and the tools needed to install the said device, for the alignment and fixation of cranial bone fragments.

In cases of bone fragmentation where bone fixation is desired, the appropriate alignment of the bone is also a desired result. This is especially true in the cranium, where bone fragmentation can occur as a result of trauma, congenital deformity, or of surgical intervention. In the field of neurosurgery, cranial bone fragments are frequently cut and removed to create defects to allow for access into the cranial cavity and the brain.

The bony cranium is generally regarded to have two surfaces: the outer surface which is characterized by the outer cortex of the bone and is adjacent to the scalp and soft tissue; and the inner surface which is characterized by the inner cortex of the bone and which is adjacent to the cranial cavity and the brain. Between the inner cortex and the outer cortex, which are dense layers of bone, lies the medullary layer which generally consists of soft bone and bone marrow. When a bone fragment is created, a cut between the bone fragment (the primary bone zone) and the remainder of the cranium (the secondary bone zone) is present.

Several methods of alignment and fixation of primary and secondary bone zones are known. Traditional techniques involve the use of several pieces of filament, such as wire, that are tied after being threaded through holes drilled obliquely through the outer cortex to the cut surface of both bone zones. Precise alignment of the two zones can be difficult and the technique can be cumbersome.

Commonly, the zones of bone can be aligned and fixated with a system of plates and screws (U.S. Pat. Nos. 5,372,598; 5,413,577; and 5,578,036). A plate made of metal or other substance can be fixated to the outer cortex of the primary bone zone with screws whose penetration of the bone can be limited to the outer cortex. With three of more plates attached to the primary bone in such a way that the plates protrude beyond the edges of the primary bone zone, the primary bone zone can be introduced into a defect and aligned to the outer cortex of the secondary bone zone without danger of the primary bone zone falling too deeply into the defect in the secondary bone zone and exerting pressure on the underlying tissue such as the brain. Fixation can then be achieved by employing additional screws fixating the plates to the outer cortex of the secondary bone zone. Plates and screws systems are believed to be the only devices currently in use that allow for the alignment and fixation of the zones, while preventing the primary bone zone from falling below the level of the secondary bone zone without actually introducing a component of the device below the secondary bone zone. Plate and screw systems can be expensive and time consuming to use.

Devices that align the two bone zones by way of compressing them between the two disks positioned along the inner and outer cortex have been described. (Foreign Patents: DE 19603887C2, DE 19634699C1, DE 29812988U1, EP 0787466A1.) A pin connects the two disks aligning and securing two bone zones. These devices introduce foreign material that is left below the inner cortex, and they do not protect the underlying tissue from compression during the installation procedure.

Devices that fixate bone zones using friction forces created by a cam without a component that extends below the inner cortex are known and described (Patent DE 19634697C1). These devices also do not protect the brain from compression during the installation procedure.

Intramedulary pins are well known in the orthopedic fields for alignment of long bones. Such pins have also been described for cranial fixation; however, the bone zones can not be aligned in three dimensions with this technique.

There is a need for an alignment and fixation device that is simple and rapid to use, versatile, and ultimately cost effective.

OBJECTS OF THE INVENTION

The object of the invention is to provide a device and instruments for its use that aligns the one cortex of a primary zone with one cortex of a secondary bone zone without extending to the opposing cortex, and which fixates the bone zones to each other. When used in the field of neurosurgery, the device is applied to the primary bone zone and it aligns the outer cortex of the primary bone zone with the outer cortex of the secondary bone zone; it prevents the primary bone zone from entering the cranial cavity; and it provides fixation of the two bone zones. The alignment feature can be used independently from the fixation feature. An example of the use of the alignment feature is in the replacement of a cranial bone fragment which will be held in place by the tissue forces of the scalp, which allows for the bone fragment to be elevated away from the cranial cavity in cases where brain swelling occurs. Fixation can also be applied to attach the alignment device to the bone, using elements alone or in combination such as filaments, screws, rivets, pins, clips, cams, friction or adhesives. The alignment aspect of the invention can also be applied to situations where it is desired to offset the alignment of the bone fragment to the adjacent bone such as where the object is to create a more prominent chin by cutting the bone of the chin and advancing the bone fragment.

The fixation feature of the invention is likewise independent from the alignment feature. The fixation feature of the device relies on the principle that the device is fixated to the primary bone zone and the fixation feature grips the secondary bone zone by mans of spring loaded tab or hook elements engaging the soft areas of the medullary space, irregularities along the cut surface, or a slot cut into the cut surface of the secondary bone zone.

SUMMARY OF THE INVENTION

The invention provides an improved clip, and method of its use, meeting the above need or needs.

As will be seen, the preferred clip is configured to interconnect primary and secondary bone zones having edges spaced apart by a gap, the clip comprising a) a tab to extend over a surface or surfaces of at least one of said bone zones, above a level defined by the one surface, and b) a first projection carried by the tab and having a hook to engage a bone zone at its edge, and below a portion of the tab that extends over the projection.

As will be seen, the projection typically extends angularly downwardly from the tab at an angle between 50° and 60° from a plane defined by the tab, and terminates at the hook, and the hook has a sharp terminal to enable penetration of bone marrow. The projection has a shank that tapers toward the hook, to provide increased bending resilience in a direction toward the hook. Also, the tab typically contains a through hole to receive a fastener that fastens to one of the bone zones; and the tab may be elongated to bridge portions of both the primary and secondary bone zones.

It is another object to provide a clip configuration incorporating a second projection carried by the tab and having a hook to engage the primary bone zone at its edge, and below said front level. Further, the two projections may advantageously extend in generally parallel relation, and angularly downwardly from the tab, and terminate at said hooks, whereby bending forces generated by deflection of both projections are utilized to achieve enhanced holding by the two hooks to the same edge of the bone zone.

Yet another object is to provide a tab retraction notch, or two retraction notches proximate the ends of the projections closest to the tab; and an alignment protrusion may be provided to be integral with the tab and located between the first and second projections for engagement with an edge of one bone zone. Also, one of the bone zones may typically comprise a bone flap removed from a cranium.

An additional object is to provide an improved method for attaching primary and secondary bone zones having edges, the method including the steps:

a) providing a tab to extend over a surface or surfaces of at least one of said bone zones, above a level defined by the one surface, b) providing a projection to be carried by the tab and to have a hook to engage a bone zone at its edge, and below said first level, c) and causing the projection to form a cantilever configuration which is resiliently deflected by hook engagement with one of the bone zone edges.

An additional step may comprise fastening the tab to at least one of the bone zones.

Where two projections are employed, the method includes the steps a) providing a tab to extend over a surface or surfaces of at least one of said bone zones, above a level defined by the one surface, b) providing tab projections to be carried by the tab and to have hooks to engage a bone zone at its edge, and below said first level, c) and causing each projection to form a cantilever configuration which is resiliently deflected by hook engagement with one of said edges.

These and other objects and advantages of the invention, as well as the details of an illustrative embodiment, will be more fully understood from the following specification and drawings, in which:

DRAWING DESCRIPTION

FIG. 5 is a side elevation showing an improved clip, with a retention projection projected downwardly at an angle from the clip top plate or tab;

FIG. 6 is an end view taken on lines 6—6 of FIG. 5;

FIG. 7 is a bottom plan view taken on lines 7—7 of FIG. 5;

FIG. 8 is a perspective view of the FIG. 5 clip; and

FIG. 9 is a section showing two FIG. 5 clips holding opposite ends of a bone flap to primary and secondary bone zones.

DETAILED DESCRIPTION

Figure 1:
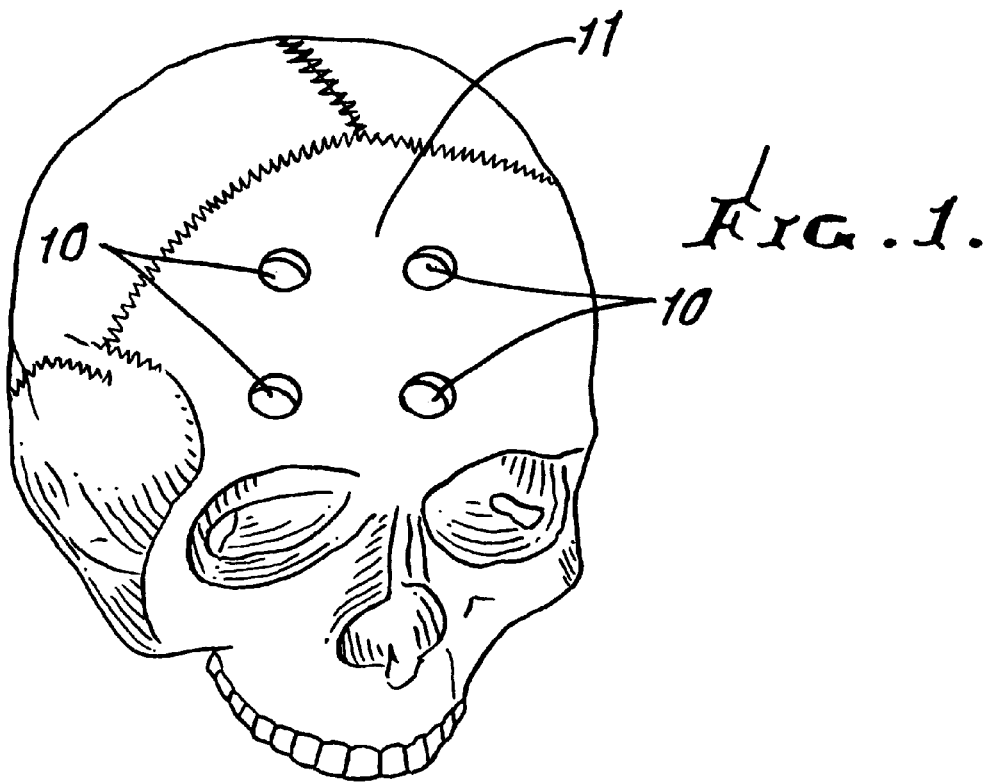
FIG. 1 is a view of a skull, showing drilled openings in the cranium arranged in a generally rectangular pattern.
Figure 2:
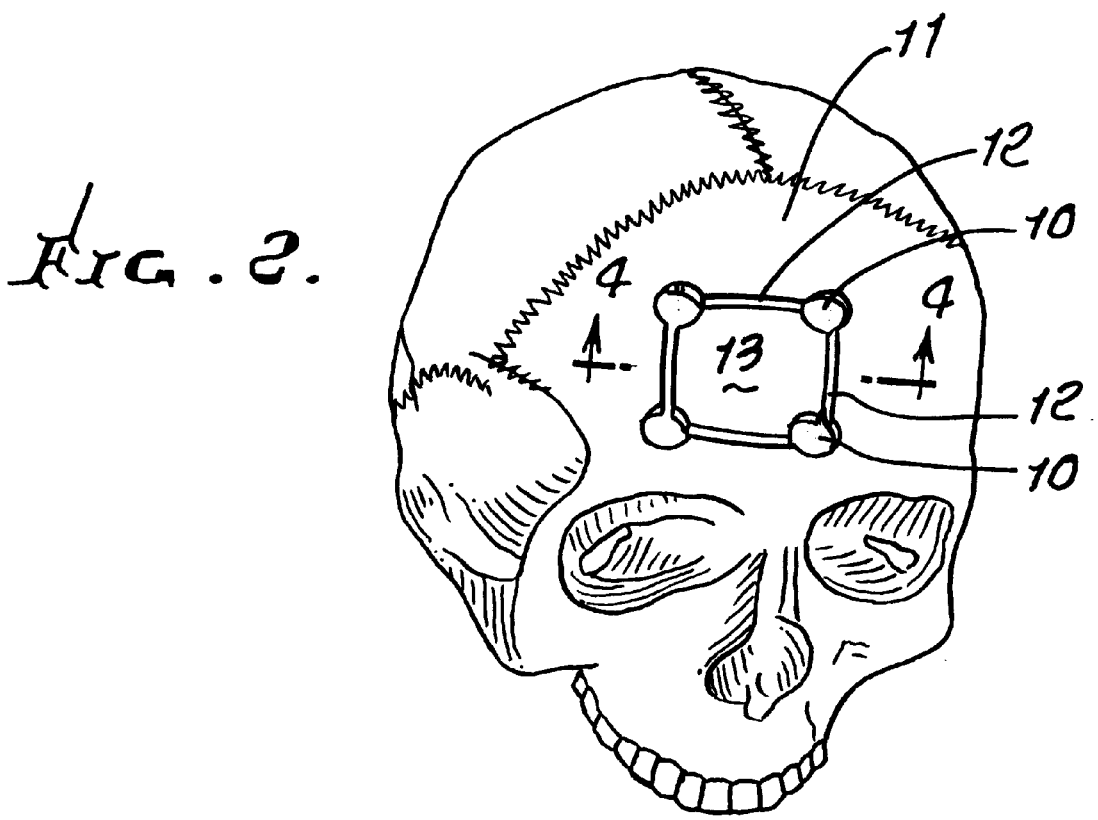
FIG. 2 is a fragmentary view showing slots formed between the FIG. 1 drilled openings.
Figure 3:
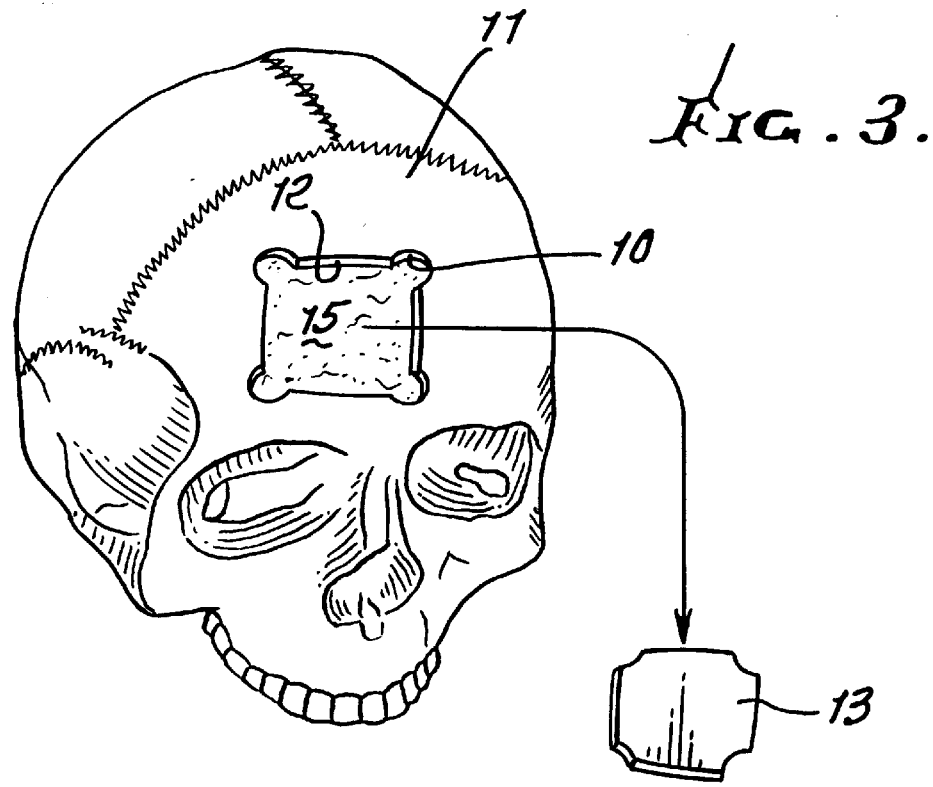
FIG. 3 is a fragmentary view showing a bone flap removed from the FIG. 2 skull cranium.

FIG. 1 shows the formation of holes 10 (for example four) in the cranium 11, as for example during brain surgery. FIG. 2 shows interconnection of the holes by cuts 12 in the cranium, to form the perimeter of a primary bone flap 13; and FIG. 3 shows removal at 14 of the flap, serving to expose the brain 15 for surgery.

Figure 4:
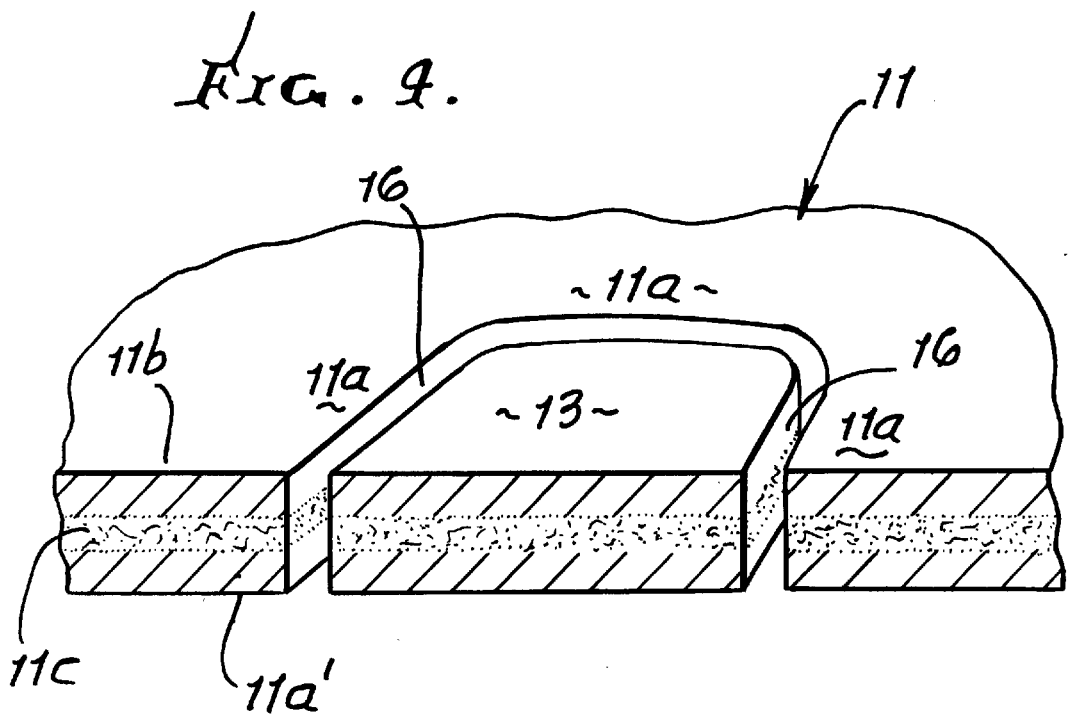
FIG. 4 is an enlarged perspective view taken in section, as on lines 4—4 of FIG. 2, to show the bone flap surrounded by a gap, in the cranium.

FIG. 4 shows, in perspective and enlarged section form, a gap 16 formed by cuts through the skull, the flap 13, and the skull secondary bone zone 11a extending adjacent the gap. Also depicted are inner and outer cortex portions 11a and 11b of the skull, and the medullary layer (soft bone and marrow) 11c between 11a and 11b, and used for flap retention purposes as will appear.

The preferred clip of the invention is seen at 20 in FIGS. 5–9, and is employed to interconnect primary and secondary bone zones 11 and 13, proximate the gap 16. The clip includes:

a) a tab 21 such as a plate configured to extend over a surface such as at 22, or surfaces, of at least one of the bone zones, above a level 22a defined by that one surface, and b) a first projection as at 23 carried by the tab, and having a hook 23a to engage bone zone 11 at its edge and below said first level. See for example edge 11d of the skull, facing the gap 16, in FIG. 9.

The projection 23 typically extends angularly downwardly from the underside of the tab toward the hook, as for example at an angle a of between 50° and 60° relative to the plane 21a of tab 21, as seen in FIG. 5; and the hook 23a tapers in a direction 24, generally normal to the elongation direction 25 of the projection 23, whereby the sharp ended hook is well adapted to hook into the medullary layer 11c of the skull. Also, the projection 23 tapers in direction 25 toward the hook whereby its lower extent is more resilient, and it flexes (see FIG. 9) as the projection is displaced downwardly in gap 16, allowing the hook to accommodate to and gouge into the exposed medullary layer, with force at least in part generated by such flexing. Note in FIG. 5 that the horizontal component of the unflexed hook length exceeds the width "w" of the gap.

FIG. 9 shows how controlled flexing of two or more projections 23 is created, as they fit down into the gap 16 extents 16a and 16b at generally opposite ends 13a and 13b of the flap 13. The interference fit is such as to flex both projections 23, particularly at their lower narrower extents, as shown, whereby the gap extents 16a and 16b are kept approximately equal.

It will be noted that the projection 23 has a shank 23b that tapers toward the hook, the uppermost end of the projection being integral with the underside 21c of the tab 21, and at the side of the gap closest to the end or edge 13a of the flap 13. A spacer 30 is shown in FIGS. 5–7 protruding downwardly from the tab, to engage flap edge 13a, to locate the clip relative to the flap 13, at the time of clip attachment to the top surface of the flap. See for example the screw 32 in FIG. 9, projecting in hole 33 in the tab, and attaching it to the flap. Other means of attachment can be provided, one example being a bonding agent.

The tab 21 extends at 21d over the flap (for example the primary bone zone) and at 21e over the cranium nearest the gap (the secondary bone zone). Tab retraction notches appear at 75 at tab opposite edges, and proximate at least one projection.

FIGS. 5–8 also show the provision of a second projection 123, like projection 23, but laterally spaced from 23. The two projections align themselves and bend relative to edge 11*d*, as they are installed so that hooks 23*a* and 123*a* engage that bone to best "bite effect".

Note the tapering opposite faces 23*f* and 23*g* of the projection 23 as seen in FIG. 5, and the tapering opposite edges 23*h* and 23*i* of the projection 23 as seen in FIGS. 6 and 7. Projection 123 is similarly bidirectionally tapered.

The method of clip attachment, includes
- a) providing a tab to extend over a surface or surfaces of at least one of said bone zones, above a level defined by the one surface,
- b) providing a projection formed to be carried by the tab and to have a hook to engage a bone zone at its edge, and below said first level,
- c) the projection formed to have a cantilever configuration which is resiliently deflected by hook engagement with one of said edges.

The method is also applicable to use of two projections 23 and 123.

I claim:

1. A clip to inter-connect primary and secondary bone zones having edges, comprising in combination:
   - a) a tab to extend over a surface or surfaces of at least one of said bone zones, above a level defined by the one surface, and
   - b) a first projection carried by the tab and having a hook to engage a bone zone at its edge, and below a portion of said tab that extends over the projection,
   - c) said projection extending angularly downwardly along its length and away from the tab at an angle between about 50° and 60° from a plane defined by the tab, and terminating at said hook,
   - d) said projection having a thickness which decreases in a direction along the projection length and toward the hook, the hook protecting sidewardly of the projection, at the end thereof,
   - e) said projection and hook both everywhere located beneath the tab,
   - f) the hook having an underside that tapers upwardly toward a plane defined by the tab.

2. The combination of claim 1 wherein the hook has a sharp terminal angled to enable penetration of bone marrow, and said projection has a shank that tapers toward the hook, to provide increased bending resilience in a direction toward the hook.

3. The combination of claim 1 including a through hole in the tab to receive a fastener that fastens to one of said bone zones.

4. The combination of claim 1 wherein the tab is elongated to bridge portions of both the primary and secondary bone zones.

5. The combination of claim 1 including a fastener carried by the tab to fasten the tab to a cranial bone flap.

6. The combination of claim 1 including a second projection carried by the tab and having a hook to engage the said one bone zone at its edge, and below said level.

7. The combination of claim 7 wherein said first and second projections extend in generally parallel relation, and angularly downwardly from the tab, and terminate at said hooks.

8. The combination of claim 1 wherein the tab has at least one retraction notch proximate the end of the first projection closest to the tab.

9. The combination of claim 7 wherein the tab has retraction notches proximate the ends of said projections closest to the tab.

10. The combination of claim 7 including an alignment protrusion integral with the tab, and located between the first and second projections for engagement with an edge of the primary bone zone.

11. The combination of claim 1 including said primary and secondary bone zones defining a gap between edges thereof, said projection defining a cantilever configuration which is resiliently deflected by hook engagement with one of said edges.

12. The combination of claim 11 wherein one of said bone zones is a bone flap removed from a cranium.

13. The combination of claim 7 including said primary and secondary bone zones defining a gap between edges thereof, each projection defining a cantilever configuration which is resiliently deflected by hook engagement with at least one of said edges.

14. The combination of claim 13 wherein one of said bone zones is a bone flap removed from a cranium.

15. The method of clip attaching primary and secondary bone zones having edges, that include:
   - a) providing a tab to extend over a surface or surfaces of at least one of said bone zones, above a level defined by said surface,
   - b) providing a projection to be carried by the tab and to have a hook to engage one of said bone zones at its edge, and below said level,
   - c) the projection formed to have a cantilever configuration which is resiliently deflected by hook engagement with one of said edges,
   - d) the projection located to extend angularly downwardly along its length and away from the tab at an angle between about 50° and 60° from a plane defined by the tab, and terminating at said hook,
   - e) the projection formed to have a thickness which decreases in a direction along the projection length and toward the hook, the hook projecting sidewardly of the projection, at the end thereof,
   - f) the projection and hook both everywhere located beneath the tab,
   - g) the hook formed to have an underside that tapers upwardly toward a plane defined by the tab.

16. The method of claim 15 wherein one of said bone zones is a bone flap previously removed from a cranium.

17. The method of claim 15 including fastening said tab to at least one of the bone zones.

18. The method of clip attaching primary and secondary bone zones, that includes:
   - a) providing a tab to extend over a surface or surfaces of at least one of said bone zones, above a level defined by said at least one of said zones,
   - b) providing a tab projection to be carried by the tab and to have a hook to engage a bone edge zone, and below said level,
   - c) and forming the projection to have a cantilever configuration which is resiliently deflected by hook engagement with said edge zone,
   - d) the projection located to extend angularly downwardly along its length and away from the tab at an angle between about 50° and 60° from a plane defined by the tab, and terminating at said hook,
   - e) the projection formed to have a thickness which decreases in a direction along the projection length and toward the hook, the hook projecting sidewardly of the projection, at the end thereof, f) the projection and hook both everywhere located beneath the tab, g) the hook formed to have an underside that tapers upwardly toward a plane defined by the tab.

19. The method of claim 18 wherein one of said bone zones is a bone flap previously removed from a cranium.

20. The method of claim 18 including fastening said tab to at least one of the bone zones.

* * * * *